United States Patent
Khalaj et al.

(10) Patent No.: US 9,931,465 B2
(45) Date of Patent: Apr. 3, 2018

(54) COMPACT FLOW REGULATING DEVICE

(71) Applicant: AVENT, INC., Alpharetta, GA (US)

(72) Inventors: Steve S. Khalaj, Laguna Hills, CA (US); Vincent A. Turturro, Milton, GA (US); Roger D. Massengale, Mission Viejo, CA (US); John A. Rotella, Lake Forest, CA (US)

(73) Assignee: Avent, Inc., Alpharetta, GA (US)

( * ) Notice: Subject to any disclaimer, the term of this patent is extended or adjusted under 35 U.S.C. 154(b) by 476 days.

(21) Appl. No.: 14/289,967

(22) Filed: May 29, 2014

(65) Prior Publication Data

US 2015/0343140 A1 Dec. 3, 2015

(51) Int. Cl.
*A61M 5/168* (2006.01)
*A61M 5/142* (2006.01)
*A61M 5/14* (2006.01)

(52) U.S. Cl.
CPC ........ *A61M 5/16804* (2013.01); *A61M 5/142* (2013.01); *A61M 5/14244* (2013.01); *A61M 5/16877* (2013.01); *A61M 5/141* (2013.01)

(58) Field of Classification Search
CPC .. A61M 5/141; A61M 5/142; A61M 5/14244; A61M 5/16804; A61M 5/16813; A61M 5/16877
See application file for complete search history.

(56) References Cited

U.S. PATENT DOCUMENTS

| | | | |
|---|---|---|---|
| 4,468,221 A * | 8/1984 | Mayfield | A61M 5/14244 128/DIG. 12 |
| 6,892,755 B2 | 5/2005 | Black | |
| 7,445,072 B2 | 11/2008 | Mabry et al. | |
| 7,661,440 B2 | 2/2010 | Mabry et al. | |
| 7,892,213 B2 | 2/2011 | Walborn | |
| 2004/0168723 A1* | 9/2004 | Black | A61M 5/152 137/505.35 |
| 2006/0070669 A1* | 4/2006 | Mabry | A61M 5/16877 137/625.18 |
| 2009/0209933 A1* | 8/2009 | Zylberberg | A61B 5/153 604/408 |
| 2011/0144586 A1* | 6/2011 | Michaud | A61M 5/1413 604/151 |
| 2011/0178461 A1* | 7/2011 | Chong | A61M 5/158 604/151 |
| 2012/0059311 A1* | 3/2012 | Gilbert | A61M 15/009 604/26 |

FOREIGN PATENT DOCUMENTS

WO  WO 2005/058394 A1  6/2005

OTHER PUBLICATIONS

International Search Report and Written Opinion for International Application PCT/US2015/031342, dated Aug. 18, 2015, 11 pages.

* cited by examiner

*Primary Examiner* — Kami A Bosworth
(74) *Attorney, Agent, or Firm* — Dority & Manning, P.A.

(57) ABSTRACT

There is provided a compact flow restriction device having a housing and tubing, the housing holding the tubing within it, the tubing reducing liquid pressure from a higher pressure at a first tubing end to a second pressure at a second tubing end, the housing adapted to be worn by a patient and the liquid delivered to said patient at the second end at the second pressure.

13 Claims, 5 Drawing Sheets

COMPACT FLOW REGULATING DEVICE

This disclosure relates to apparatus or equipment for regulating the flow rate of liquids that are administered at very low rates.

Clogging is a known problem for tubes used in liquid delivery systems, particularly for systems in which the flow rate is very low or in which there are temperature fluctuations that may affect the stability of the liquid being measured. In addition to clogging, the mere measurement of very low flow rates requires meticulous attention to the manufacturing process as pressure differentials are low and clearances and tolerances are especially small.

The uses for the flow restricting devices for very low flow rates are many; including in the medical field in the administration of drugs, the process chemical field for the injection of particular additives to mixtures, in food processing, and many others. In the medical field in particular, low flow dispensation is useful for constant administration of drugs for treatment of chronic conditions, e.g. pain.

It would be of great benefit to have a flow regulating device that is accurate, relatively independent of temperature and that did not easily clog. It would be of added benefit if the device were easy to assemble and compact so that it was inconspicuous when worn by a patient for medical use, for example.

SUMMARY

The present disclosure addresses the problems described above by providing a compact, low flow regulating device. The device has a housing and tubing, the housing holding the tubing within it, the tubing reducing liquid pressure from a higher pressure at a first tubing end to a second pressure at a second tubing end, the housing adapted to be worn by a patient and the liquid delivered to said patient at the second end at the second pressure.

Other objects, advantages and applications of the present disclosure will be made clear by the following detailed description.

BRIEF DESCRIPTION OF THE DRAWINGS

These and other features of this disclosure will be more readily understood from the following detailed description of the various aspects of the disclosure taken in conjunction with the accompanying drawings in which.

DETAILED DESCRIPTION

Figure 1:
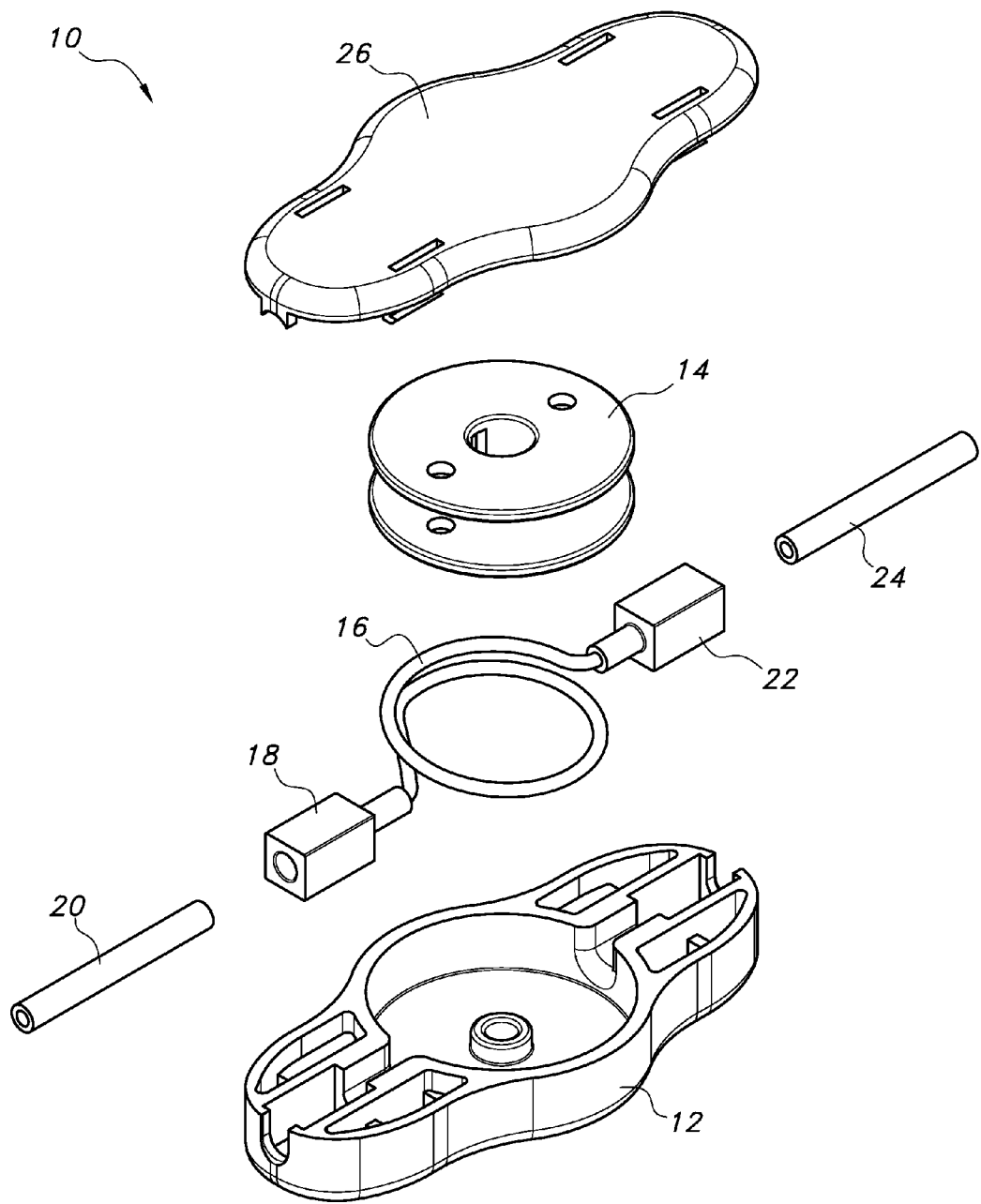
FIG. 1 is an illustration of the parts of the flow measurement device, including the housing, top, spool, connector tubing and connectors.

Reference will now be made in detail to one or more embodiments, examples of which are illustrated in the drawings. It should be understood that features illustrated or described as part of one embodiment may be used with another embodiment to yield still a further embodiment. It is intended that the claims include these and other modifications and variations as coming within the scope and spirit of the disclosure.

The present disclosure addresses the problems described above by providing a compact, flow regulating device.

According to Poiseuille's law, the velocity of the steady flow of a fluid through a narrow tube (as a blood vessel or a catheter) varies directly as the pressure and the fourth power of the radius of the tube and inversely as the length of the tube and the coefficient of viscosity. The Poiseuille equation may be expressed as:

$$Q = \Delta P \pi r^4 / 8 \mu L$$

where:
ΔP is the pressure loss
L is the length of pipe
P is the dynamic viscosity
Q is the volumetric flow rate desired
r is the radius
π is the mathematical constant Pi (3.14159)

If one assumes a constant input pressure to the tube, using, for example, a controlled (fixed) pump discharge pressure and a tube discharge pressure of approximately zero gage (atmospheric pressure or less than 0.5 psig, more particularly less than 0.25 psig and still more particularly less than 0.1 psig), the equation can be solved for L. In the table below, the first four columns provide the input variables for the equation in English units and the last column the computed L needed. Conversion of units may be necessary and may be done by one skilled in the art.

| (Q) Flow rate desired ml/hr | (P) Pressure lb/in² | (2r) Diameter (in) | (μ) Viscosity lb · sec/ft² | Computed Length (in) |
|---|---|---|---|---|
| 10 | 6 | 0.00265 | 2.05E–05 | 0.301 |
| 9 | 6 | 0.00265 | 2.05E–05 | 0.334 |
| 8 | 6 | 0.00265 | 2.05E–05 | 0.376 |
| 7 | 6 | 0.00265 | 2.05E–05 | 0.430 |
| 6 | 6 | 0.00265 | 2.05E–05 | 0.502 |
| 5 | 6 | 0.00265 | 2.05E–05 | 0.602 |
| 4 | 6 | 0.00265 | 2.05E–05 | 0.752 |
| 3 | 6 | 0.00265 | 2.05E–05 | 1.003 |
| 2 | 6 | 0.00265 | 2.05E–05 | 1.505 |
| 1 | 6 | 0.00265 | 2.05E–05 | 3.010 |
| 0.5 | 6 | 0.00265 | 2.05E–05 | 6.019 |

As can be seen from the table, low flow rates require a lengthy tube or, of course a tube of a smaller diameter with its associated higher pressure drop. As noted above, however, a smaller diameter tube poses much greater problems with clogging, especially with a higher viscosity fluid. For this reason, a larger diameter tube is desired. A larger diameter tube must be much greater in length, however, to achieve the same pressure drop. Tethering a patient to a long tube for long term administration of a drug presents problems in patient mobility. Administration of a drug for pain management, for example, is often done on a continuous basis. Immobilizing an otherwise ambulatory patient for long periods of time is not desirable and may not be tolerable by the patient. Another solution is necessary.

One way of overcoming the problem of using a long length of tubing is to provide a compact device that may be worn by the user against his body. This provides the added benefit of maintaining the drug to be dispensed at a relatively constant (body) temperature and therefore a constant viscosity and dispensing rate. The compact device provided herein allows the patient to be ambulatory yet to receive the prescribed medication on a continuous basis.

FIG. 1 provides an exploded view of the parts of the device 10, including the housing 12, spool 14, flow tubing 16, tube connectors 18, 22 and tubing 20, 24. Also illustrated is the housing top 26. The spool 14 is shown separately as well as within the housing 12.

Figure 2:
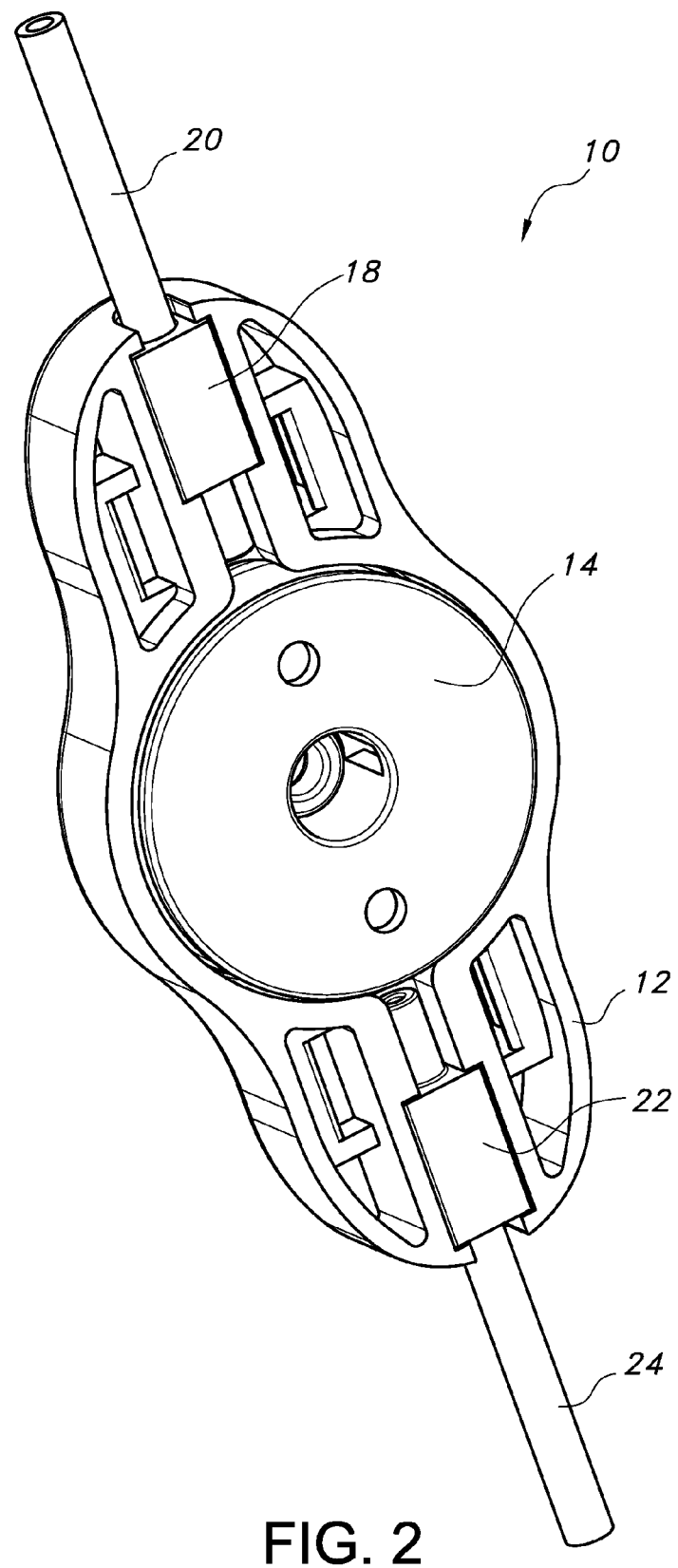
FIG. 2 is an illustration of the device from above, with the top removed to reveal the installed spool with the connectors and connector tubing visible.

FIG. 2 shows a view from above the device 10 with the top 26 removed. The flow tubing 16 is not present in this view. The relationship of the housing 12 to the spool 14 is clearly visible. As well, the relationship of the tubing connectors 18, 22 to the housing 12 and to the tubing 20, 24 is clearly visible.

Figure 3:
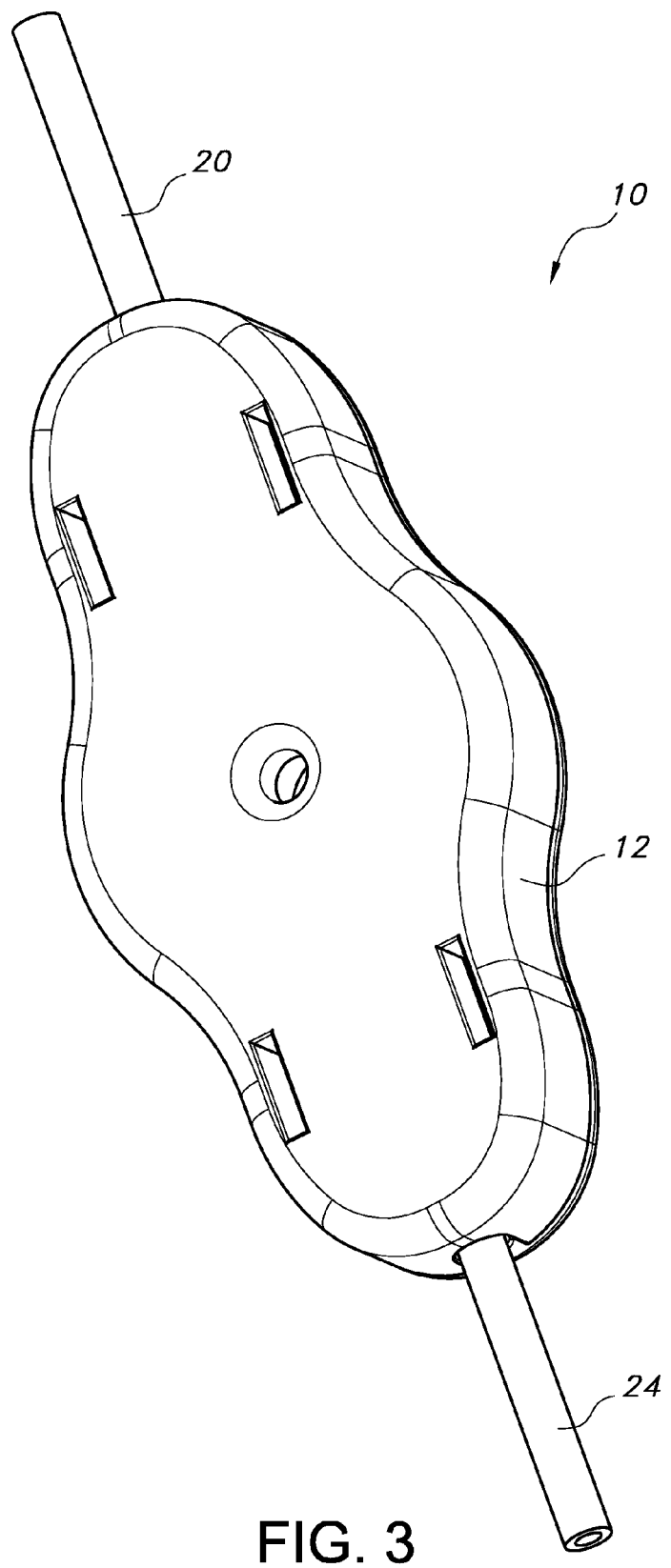
FIG. 3 is an illustration of the device from below, showing the bottom of the housing and the connector tubing.

FIG. 3 shows the back of the device 10. The housing 12 is visible along with the tubing 20, 24.

Figure 4:
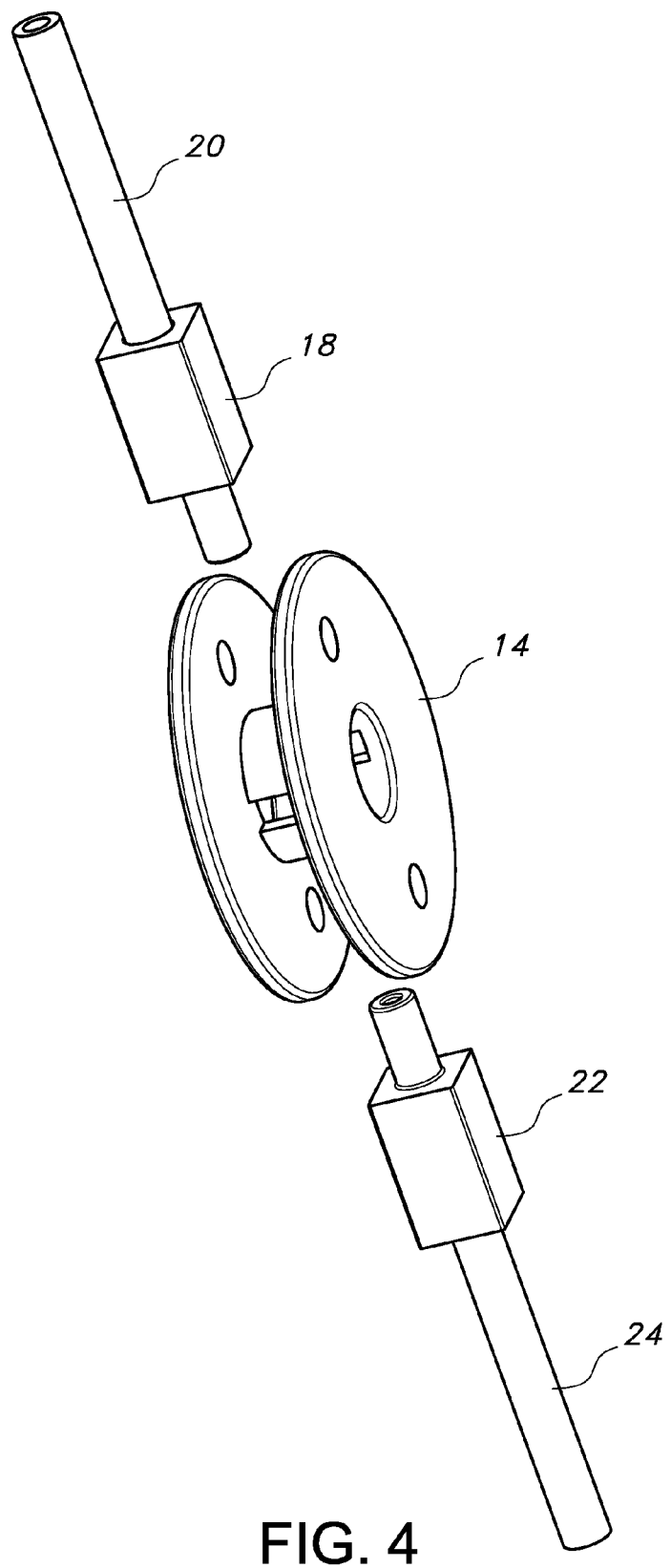
FIG. 4 is an illustration of the device showing the spool, connectors and connector tubing prior to assembly.

FIG. 4 shows the approximate relationship between the spool 14, tubing connectors 18, 22 and tubing 20, 24 without the housing 12, top 26 or flow tubing 16.

Figure 5:
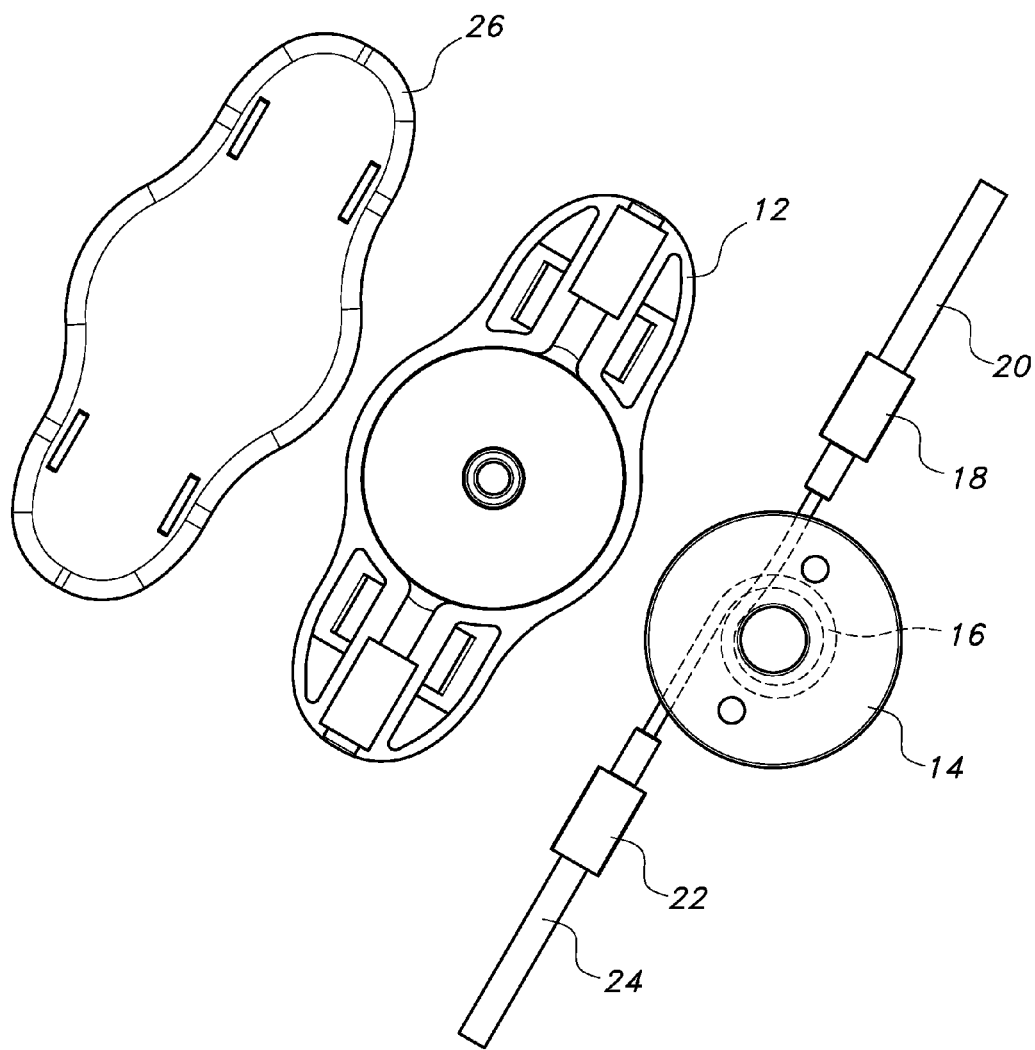
FIG. 5 is an illustration of the spool with the flow tubing installed, connectors and connector tubing as well as the housing and top.

FIG. 5 shows the separated top 26 and housing 12. This figure also shows the assembled spool 14 holding the flow tubing 16 wrapped around the spool 14. The flow tubing 16 connects to the tubing connectors 18, 22 on either end, which then in turn connect to the tubing 20, 24.

Example 1

Turning to the table above, if a flow rate of 0.5 ml/hour of a fluid with a viscosity of 0.0000205 lb.sec/ft$^2$ is desired from a pump with a discharge pressure of 6 psig, tubing of 0.00265 inches ID and about 6 inches in length should produce the requisite flow rate.

Example 2

Turning to the table above, if a flow rate of 5 ml/hour of a fluid with a viscosity of 0.0000205 lb.sec/ft$^2$ is desired from a pump with a discharge pressure of 6 psig, tubing of 0.00265 inches ID and about 0.6 inches in length should produce the requisite flow rate.

Stated more generally from the principles of the Poiseuille equation and the table; there is disclosed herein a compact flow restriction device that delivers a liquid flow rate of between 0.5 ml/hour and 10 ml/hr of a fluid from a pump with a discharge pressure of between 3 and 15 psig, the liquid flowing through tubing of between 0.001 to 0.01 inches ID and of between about 0.3 and 6 inches in length. The device has a housing adapted to be worn by a patient and the liquid is delivered to the patient at approximately atmospheric pressure.

The device may be of varying sizes provided it accommodates the desired length of tubing and may be successfully worn by a patient. In one embodiment the device is about 2 inches in length, 0.75 inches wide, and 0.3 inches thick. In various embodiments the inner diameter of the tubing can be from 0.001 inches to 0.01 inches, more particularly between 0.002 inches and 0.005 inches. While it is true that a smooth or rough tube interior will affect flow somewhat, the velocities of flow are generally so low as to be laminar and so are relatively unaffected by the roughness of the tube interior.

It should also be noted that although tubing wound around a spool is illustrated, the tubing may be assembled in other configurations without a spool. This could include the tubing being laid back and forth into the housing like a ribbon, placing it in a circular configuration without a spool, or laying it in the housing in a figure eight configuration. The device may also have a spool with a slotted hub so that the middle of the tube can be inserted into the spool and the spool spun so that it winds the tubing onto the hub in either direction.

Materials of construction for the tubing and the device generally (e.g. housing, spool, tubing) can be metals or plastics. Stamped metal may be used for the housing, for example, for better heat transfer from the body than plastic. Plastic includes PVC, polypropylene, polyethylene, nylon, TEFLON®, poly carbonate, and other common plastics. Moreover, all parts of the device need not be made from the same material. As noted above, the housing may be made of metal or other heat conducting material for improved heat transfer and the spool and tubing may be plastic, since this compact device may be worn by the user against his body. In this manner, this device provides the added benefit of maintaining the drug to be dispensed at a relatively constant temperature and therefore a constant viscosity and dispensing rate. The housing may have a volume that allows for an insulating effect from the ambient air temperature by simply using still air. The housing may alternatively be filled with foam (e.g. closed celled foam) to surround the spool and tubing and provide insulation from ambient temperature variations as well.

While the present invention has been described in connection with certain preferred embodiments it is to be understood that the subject matter encompassed by way of the present disclosure is not to be limited to those specific embodiments. On the contrary, it is intended for the subject matter of the invention to include all alternatives, modifications and equivalents as can be included within the spirit and scope of the claims.

What is claimed is:

1. A compact flow restriction device, comprising:
   a housing adapted to be worn by a patient;
   a single flow tubing within the housing;
   a first tubing extending from a first end of the housing; and
   a second tubing extending from a second end of the housing,
   wherein the flow tubing is directly connected to the first tubing by a first connector,
   wherein the flow tubing is directly connected to the second tubing by a second connector,
   wherein the flow tubing is configured to reduce a pressure of a liquid flowing in the flow tubing from a pump discharge pressure at the first tubing to approximately atmospheric pressure at the second tubing,
   wherein the device is configured to deliver the liquid to the patient at approximately atmospheric pressure, and
   wherein the device is configured to deliver the liquid at a flow rate greater than 0 ml/hr and less than 1 ml/hr.

2. The compact flow restriction device of claim 1, wherein the device is configured to deliver said liquid to the patient on a continuous basis.

3. The compact flow restriction device of claim 1, wherein said flow tubing is wound around a spool within said housing.

4. The compact flow restriction device of claim 3, wherein said spool and said flow tubing are each made from plastic selected from the group consisting of PVC, polypropylene, polyethylene, nylon, TEFLON®, and polycarbonate.

5. The compact flow restriction device of claim 4, wherein said housing is made from metal.

6. The compact flow restriction device of claim 4, wherein said housing is filled with foam to surround said spool and said flow tubing to provide insulation from ambient temperature variations.

7. The compact flow restriction device of claim 1, wherein said flow tubing is laid back and forth inside the housing like a ribbon.

8. The compact flow restriction device of claim 1, wherein said flow tubing is placed in a circular configuration within said housing without a spool.

9. The compact flow restriction device of claim 1, wherein said flow tubing has an inner diameter of from 0.001 inches to 0.01 inches.

10. The compact flow restriction device of claim 1, wherein said flow tubing has an inner diameter of from 0.002 inches and 0.005 inches.

11. The compact flow restriction device of claim 1, wherein said housing is about 2 inches in length, 0.75 inches wide, and 0.3 inches thick.

12. The compact flow restriction device of claim 1, wherein the device is configured to regulate the flow rate of the liquid to about 0.5 ml/hour.

13. A compact flow restriction device, comprising:
a housing adapted to be worn by a patient;
a flow tubing within the housing;
a first tubing extending from a first end of the housing; and
a second tubing extending from a second end of the housing,
wherein the flow tubing is connected to the first tubing by a first connector,
wherein the flow tubing is connected to the second tubing by a second connector,
wherein the flow tubing is configured to reduce a pressure of a liquid flowing in the flow tubing from a pump discharge pressure at the first tubing to approximately atmospheric pressure at the second tubing,
wherein the device is configured to deliver the liquid to the patient at approximately atmospheric pressure,
wherein the device is configured to deliver the liquid at a non-adjustable flow rate of between 0.5 ml/hour and 10 ml/hr, and
wherein the flow tubing has an inner diameter of less than 0.003 inches.

* * * * *